United States Patent [19]
Jager et al.

[11] Patent Number: 5,844,006
[45] Date of Patent: *Dec. 1, 1998

[54] PROCESS FOR PRODUCING LIQUID AND, OPTIONALLY, GASEOUS PRODUCTS FROM GASEOUS REACTANTS

[75] Inventors: Berend Jager, Sasolburg; André Peter Steynberg, Vanderbijlpark, both of South Africa; Juan Ricardo Inga, Pittsburgh, Pa.; Renus Constantyn Kelfkens, Secunda, South Africa; Michael Anthony Smith; Francois Erenst Johannes Malherbe, both of Sasolburg, South Africa

[73] Assignee: Sasol Chemical Industries (Proprietary) Limited, Johannesburg, South Africa

[ * ] Notice: The term of this patent shall not extend beyond the expiration date of Pat. No. 5,

[21] Appl. No.: 719,707

[22] Filed: Sep. 27, 1996

Related U.S. Application Data

[63] Continuation of Ser. No. 187,189, Jan. 25, 1994.

[30] Foreign Application Priority Data

Jan. 27, 1993 [ZA] South Africa ............................ 93/0588

[51] Int. Cl.⁶ .............................. C07C 27/00; B01J 20/34
[52] U.S. Cl. .............................. 518/700; 518/709; 502/20
[58] Field of Search ............................ 252/373; 518/700, 518/709; 502/20

[56] References Cited

U.S. PATENT DOCUMENTS

| | | | |
|---|---|---|---|
| 2,540,706 | 2/1951 | Beck | 260/449.6 |
| 2,671,103 | 3/1954 | Kolgel | 518/700 |
| 4,413,063 | 11/1983 | Audigert | 518/700 |
| 4,472,534 | 9/1984 | Ryan | 518/700 |
| 4,529,738 | 7/1985 | Sugier | 518/700 |
| 5,324,355 | 6/1994 | Benham | 44/452 |
| 5,422,375 | 6/1995 | Rytter . | |
| 5,520,890 | 5/1996 | Loerentzen . | |
| 5,599,849 | 2/1997 | Jager . | |

FOREIGN PATENT DOCUMENTS

| | | |
|---|---|---|
| 77437 | 3/1985 | European Pat. Off. . |
| 0313375 | 4/1989 | European Pat. Off. . |
| 0412785 | 2/1991 | European Pat. Off. . |
| 446035 | 9/1991 | European Pat. Off. . |
| 450860 | 10/1991 | European Pat. Off. . |
| 450861 | 10/1991 | European Pat. Off. . |
| 0592176 | 4/1994 | European Pat. Off. . |
| 873645 | 7/1942 | France . |
| 274981 | 1/1990 | German Dem. Rep. . |
| 60-147228 | 3/1985 | Japan . |
| 9316796 | 9/1993 | WIPO . |

OTHER PUBLICATIONS

Patent Abstracts of Japan, vol. 9, No. 309 (318) Dec. 5, 1985 & JPA 60 147228 Aug. 3, 1985.

*Primary Examiner*—Gary Geist
*Assistant Examiner*—Karl J. Puttlitz, Jr.
*Attorney, Agent, or Firm*—Ladas & Parry

[57] ABSTRACT

A process for producing liquid and, optionally, gaseous products from gaseous reactants comprises feeding gaseous reactants into a slurry bed of solid particles suspended in a liquid; allowing the reactants to react as they pass upwardly through the slurry bed, thereby to form liquid and, optionally, gaseous products; and separating liquid product from the solid particles by passing, in a filtration zone within the slurry bed, liquid product through a filtration medium in a first direction, so that a cake of the solid particles forms on the filtration medium. The passage of liquid product through the filtering medium is interrupted. The filtering medium is then backflushed by passing a flushing fluid through the filtering medium in a second direction, opposite to the first direction, for at least portions of the periods that the liquid product passage is interrupted, thereby to dislodge the cake from the filtering medium.

16 Claims, 3 Drawing Sheets

PROCESS FOR PRODUCING LIQUID AND, OPTIONALLY, GASEOUS PRODUCTS FROM GASEOUS REACTANTS

This is a continuation of copending application Ser. No. 08/187,189 filed on Jan. 25, 1994.

THIS INVENTION relates to a process for producing liquid and, optionally, gaseous products from gaseous reactants. It relates also to an installation for producing liquid and, optionally, gaseous products from gaseous reactants.

According to a first aspect of the invention, there is provided, broadly, a process for producing liquid and, optionally, gaseous products from gaseous reactants, which process comprises feeding gaseous reactants at a low level into a slurry bed of solid particles suspended in a suspension liquid;

allowing the gaseous reactants to react as they pass upwardly through the slurry bed, thereby to form liquid and, optionally, gaseous products;

separating liquid product from the solid particles by passing, in a filtration zone within the slurry bed, liquid product through a filtration medium in a first direction, so that a cake of the solid particles forms on the filtration medium;

from time to time interrupting the passage of liquid product through the filtering medium; and backflushing the filtering medium by passing a flushing fluid through the filtering medium in a second direction, opposite to the first direction, for at least portions of the periods that the liquid product passage is interrupted, thereby to dislodge the cake from the filtering medium.

While it is believed that the process can at least in principle have broader application, it is envisaged that the solid particles will normally be catalyst particles for catalyzing the reaction of the gaseous reactants into the liquid product, and, when applicable, the gaseous product; and the suspension liquid will normally, but not necessarily always, be the liquid product.

Furthermore, while it is also believed that, in principle, the process can have broader application, it is envisaged that it will have particular application in hydrocarbon synthesis where the gaseous reactants are capable of reacting catalytically in the slurry bed to form liquid hydrocarbon product and, optionally, gaseous hydrocarbon product. In particular, the hydrocarbon synthesis may be Fischer-Tropsch synthesis, with the gaseous reactants being in the form of a synthesis gas stream comprising mainly carbon monoxide and hydrogen, and with both liquid and gaseous hydrocarbon products being produced.

The catalyst particles can thus be any desired Fischer-Tropsch catalyst, such as an iron-based catalyst, a cobalt-based catalyst, or any other Fischer-Tropsch catalyst. The catalyst particles may have a desired particle size range, eg no particles greater than 300 microns and less than 5% by mass of the particles being smaller than 22 microns. The catalyst particle size range may be selected, bearing in mind the filtering medium. Conversely, the filtering medium may be selected bearing in mind the catalyst particle size range.

The slurry bed can thus be provided in a suitable vessel, with unreacted reactants and gaseous product being withdrawn from the vessel above the slurry bed, and the separated liquid product also being withdrawn from the vessel. The vessel will thus be maintained at normal elevated pressure and temperature conditions associated with Fischer-Tropsch synthesis, eg a predetermined operating pressure in the range 18 to 50 bar, and at a predetermined temperature in the range 160° C. and 280° C., or even higher for the production of lower boiling point product.

The slurry bed may be characterized thereby that it, and in particular the filtration zone thereof, is not mechanically mixed or agitated, eg not mechanically stirred. The catalyst particles in the slurry bed, and in particular in the filtration zone thereof, are thus maintained in suspension by the turbulence created by the synthesis gas stream passing through the slurry bed, ie bubbling through the bed. The gas velocity through the slurry bed is thus sufficiently high to maintain the slurry bed, and in particular the filtration zone thereof, in a state of turbulence or suspension. Thus, the superficial gas velocity through the filtration zone may be between 5 and 70 cm/s, typically between 15 and 55 cm/s, based on the filtration zone open cross-sectional area.

According to a second aspect of the invention, there is provided an installation for producing liquid and, optionally, gaseous products from gaseous reactants, the installation comprising a reactor vessel having a slurry bed zone which, in use, will contain a slurry bed of solid particles suspended in a suspension liquid;

a gas inlet in the vessel at a low level within the slurry bed zone, for introducing gaseous reactants into the vessel;

a gas outlet in the vessel above the slurry bed zone, for withdrawing unreacted gaseous reactants and, when present, gaseous products from the vessel;

a filtering medium in a filtration zone located within the slurry bed zone;

liquid displacement means for displacing liquid product through the filtering medium in a first direction, while solid particles build up as a cake on the filtering medium; and backflushing means for passing a flushing fluid through the filtering medium in a second direction, opposite to the first direction, from time to time, thereby to dislodge the cake from the filtering medium.

The filtering medium may be part of a filter cartridge or element mounted in the vessel, and may be of a type which is of elongate form, with the filtering medium being of cylindrical form and enclosing a filtrate collecting zone, and with a filtrate outlet for withdrawing filtrate, ie liquid product, being provided at one end thereof.

While, in principle, the filtering medium can be any desired filtering medium having a desired opening size to prevent catalyst particles passing therethrough, it is preferably of a type with which permanent clogging or impregnation thereof with the catalyst particles does not occur. Thus, the filtering medium can be a mesh, porous material such as ceramic, perforated sheet, spiral wire wound, eg from wedge wire, or the like.

A plurality of the filter elements, located at the same or different levels within the filtration zone, may be provided. Preferably a number of the filter elements are located close to the upper surface of the slurry bed, ie the filtration zone is provided close to the upper surface of the slurry bed. The filter elements may be arranged in a plurality of banks, with each filter bank comprising a number of the filter elements.

In principle, the elements can be located at any desired inclination; however, they are preferably located vertically with their liquid product or filtrate outlets directed downwardly.

The passage of the liquid product through the filtering media may be effected by applying a pressure differential across the filtering media and any cake build-up thereon.

Preferably this pressure differential may be up to 8 bar, and is typically in the region of about 4 bar. The pressure differential may be effected by withdrawing the liquid product into a rundown vessel which is at a lower pressure than the reactor vessel, with the filtrate outlets of the filter elements being connected to the rundown vessel by means of suitable liquid product conduits. The conduits may include a primary liquid product conduit leading from the filtrate outlet of each filter element; a secondary liquid product conduit into which the primary conduits of all the filter elements of the particular bank of filter elements tie; and a tertiary liquid product conduit leading to the rundown vessel, with the secondary conduits all tying into the tertiary conduit.

The flushing fluid may be process or non-process derived liquid and/or gas, eg some of the liquid and/or gaseous product.

The backflushing may, in general, be effected in pulse-like fashion. Thus, the backflushing may comprise an initial pulse of flushing liquid and/or gas, optimally followed by one or more further pulses of flushing liquid and/or gas. Each backflushing pulse may comprise initiating backflushing rapidly, ie commencing flow of flushing fluid rapidly; and backflushing the elements rapidly with a volume of the flushing fluid. This volume of flushing fluid may be relatively large, eg approximately equivalent to the internal volume of the filter elements. It can, however, be less than the internal volume of the filter elements, eg less than half their internal volume. When the volume of flushing fluid used during the initial pulse is relatively large, the volume of flushing fluid used during a second pulse may be less than that of the initial pulse, eg less than half the internal volume of the elements. However, when the volume of flushing fluid used during an initial pulse is relatively small as hereinbefore described, then the volume of flushing fluid during a further or second pulse may be similar to that of the initial pulse. The nature of any further pulses, when utilized, and the volume of the flushing fluid used during such pulses, may be similar to those of the second pulse hereinbefore described.

The pressure differential across the filtering media and filter cake during backflushing may be up to 10 bar depending on the degree of clogging or age of the filtering media, and is typically in the region of 5 bar.

The flushing fluid flow rate may be at least 6000 l/h/m$^2$ of filtering media. Thus, the flushing fluid flow rate may be between 6000 l/h/m$^2$ of filtering media when the pressure differential across the filtering media is about 5 bar, and between about 10000 and 12000 l/h/m$^2$ when the pressure differential is about 10 bar.

The process may preferably include subjecting the filtering elements to a waiting period during which no filtering or backflushing takes place, ie during which there is no liquid flow through the filtering media of the elements, to enhance subsequent filtration. The waiting period may be between 15 and 60 minutes, or even longer, but is typically about 30 minutes.

The liquid product conduits and rundown vessel may conveniently form part of the backflushing means, with the rundown vessel then also constituting a flushing fluid vessel and the liquid product conduits constituting flushing fluid conduits; however, if desired, a separate flushing fluid vessel and flushing fluid conduit leading from the flushing fluid vessel to the secondary conduits, may be provided. The backflushing means may include at least one quick opening valve or the like, for effecting the backflushing pulses, in one of the flushing conduits; and pressurizing means for pressurizing the flushing fluid vessel. Thus, backflushing may be effected by pressurizing the flushing fluid vessel with the vessel containing some flushing liquid and/or gas, which may be product, and then actuating the quick opening valve until the desired volume of flushing liquid and/or gas has passed through the filter elements of a bank of the filter elements in the second direction. Instead of utilizing a pressurized flushing fluid vessel, a pump and/or compressor can be used for supplying the flushing fluid to the filter elements.

In particular, backflushing may be effected by propelling or forcing residual liquid product in the conduits back through the filter elements in the second direction, preferably also through a restriction orifice located in the primary conduit of each filter element, by means of pressurized gas. It has been found that cleaning of the filter element surfaces is considerably improved, thus enhancing subsequent filtering performance thereof, when backflushing with the gas is effected for at least a sufficiently long period of time to displace substantially all the residual liquid product through the restriction orifices back into the filter elements. Backflushing with gas also has the advantage that the gas thereby introduced into the reactor vessel and which is removed with the product gas, does not have to be filtered again, thereby reducing loading on the filter elements during filtration.

The invention will now be described by way of example with reference to the accompanying diagrammatic drawings.

Figure 1:
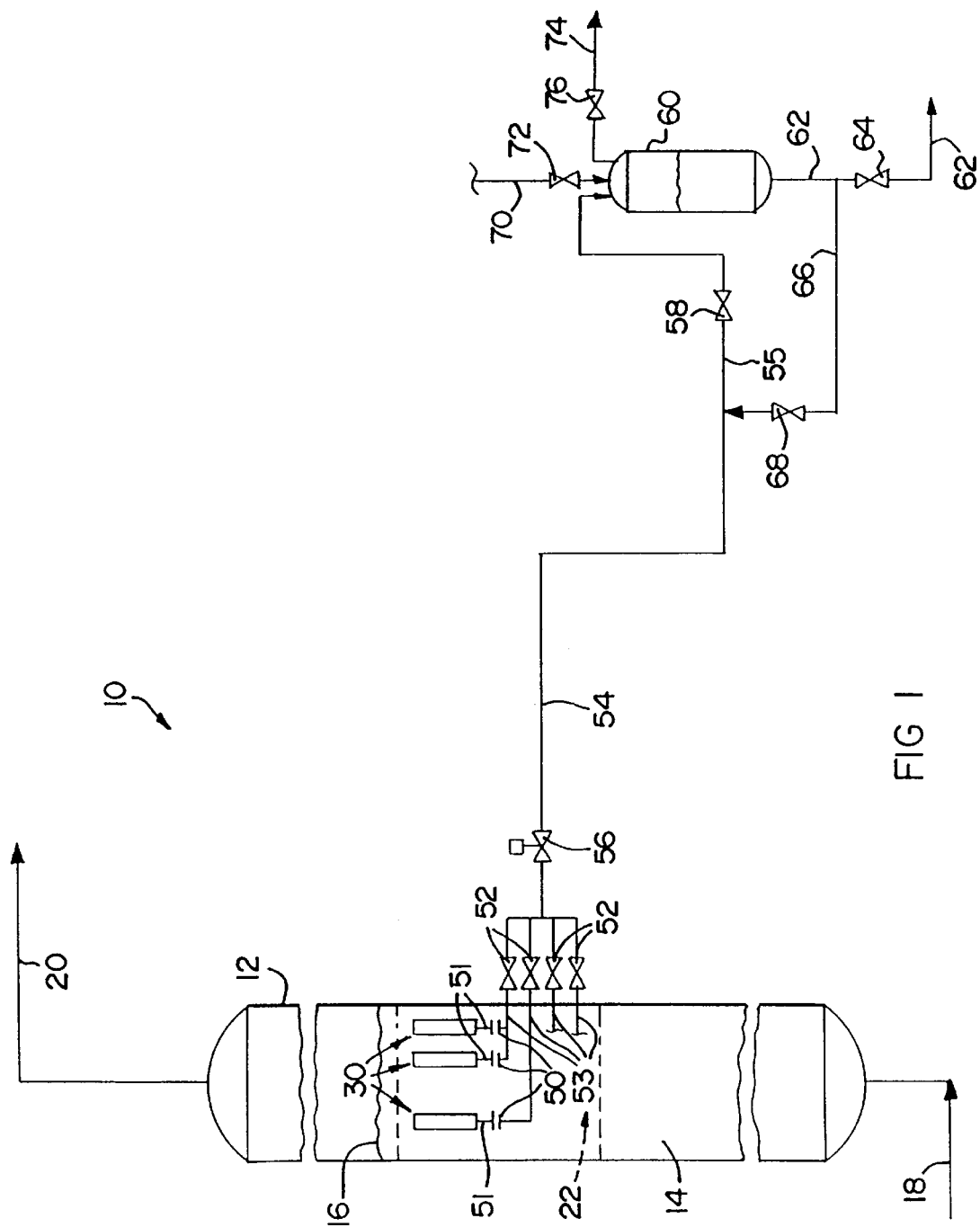
FIG. 1 shows a simplified flow diagram of a large pilot plant installation according to one embodiment of the invention, for producing gaseous and liquid products from gaseous reactants.
Figure 3:
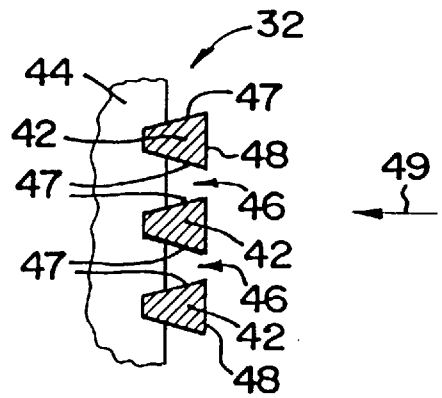
FIG. 3 shows, in part, an enlarged sectional view through III—III in FIG. 2.
Figure 2:
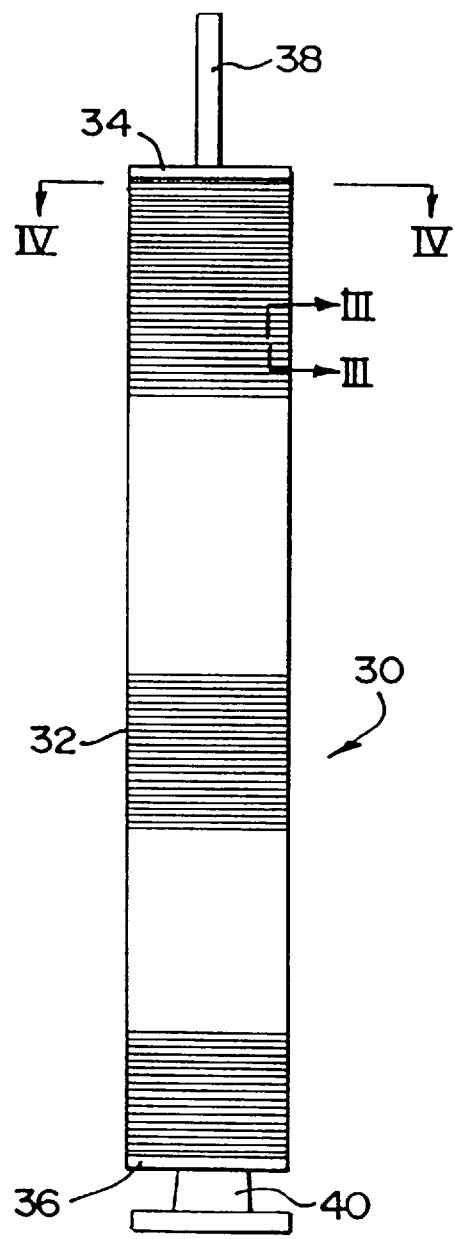
FIG. 2 shows an enlarged side view of one of the filter elements shown in FIG. 1.
Figure 4:
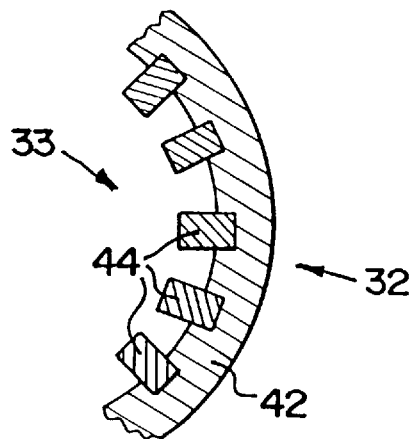
FIG. 4 shows, in part, a sectional view through IV—IV in FIG. 2.

Referring to FIGS. 1 to 4, reference numeral 10 generally indicates an installation according to one embodiment of the invention, for producing gaseous and liquid products from gaseous reactants.

The installation 10 includes an upright cylindrical Fischer-Tropsch synthesis reactor vessel 12.

The vessel 12 provides a slurry bed zone normally containing a slurry bed 14 of catalyst particles suspended in liquid product and through which gas is passing, as described in more detail hereunder. The slurry bed 14 has an upper surface 16, and the expanded height of the slurry bed 14 while gas passes through it is typically between 14 and 18 m when the total reactor length is about 24 m.

A synthesis gas flow line or conduit 18 is connected to a gas inlet (not shown) provided at the bottom of the vessel 12, while a gas withdrawal flow line or conduit 20 leads from a gas outlet (not shown) provided at the top of the vessel 12. A suitable gas distributor (not shown) is connected to the gas inlet.

The installation 10 also includes a plurality of filter elements 30 (only some of which are shown) located in a filtration zone 22 within the slurry bed 14, arranged in a plurality of banks. Each filter element 30 is of elongate cylindrical form, and comprises a cylindrical filtering medium 32 enclosing a filtrate or liquid collecting zone 33.

The medium 32 is located between end plates 34, 36. a mounting rod 38 protrudes from the end plate 34, while a flanged liquid outlet 40 is provided on the end plate 36. Thus, by means of the outlet 40, filtrate or liquid can be withdrawn from the collecting zone of the element or cartridge 30. The elements 30 are mounted in position in the vessel 12 by mens of the rod 38 and flanged outlets 40. This mounting is not shown in detail in the drawings, but is typically effected by connecting the rod 38 to a lattice or grid spanning the vessel 12, while the outlet is connected to a conduit as hereinafter described.

The filtering medium 32 comprises a spiral wound wire 42 embedded in, or attached to, circumferentially spaced elongate supports 44 extending between the end plates 34, 36. Filtration openings or slots 46 are thus provided between adjacent loops of the wire 42. The wire 42 has, adjacent the openings or slots 46, surfaces 47 which taper away from each other, in the direction of the collecting zone. The wire 42 thus also has surfaces 48 against which a cake of catalyst particles (not shown) will form, as described in more detail hereunder, when liquid product is filtered by the elements 30 as it passes through the slots 46 in the direction of arrow 49. As a result of the tapering surfaces 47, solid particles will not readily permanently clog or impregnate the openings or slots 46 when filtered product passes through in the direction of arrow 49.

Typically, the filter elements 30 have an external diameter of 11 to 12 cm, with the wire 42 being of stainless steel. The wire 42 is typically about 1,2 mm wide at its base. The width of the slots or openings 46 is typically between 0,02–0,04 mm.

Instead of the filter elements 30, any other suitable elongate filter elements or cartridges, such as ceramic or sintered metal filter elements, can be used.

The filtration zone 22 is preferably located at a high level within the slurry bed, so that the filter elements 30 are located near the upper surface 16 thereof. As a result, they will not be embedded in settled solids or catalyst on slumping of the bed 14 which will occur if the gas feed to the vessel 12 is interrupted. However, it has been found that the filtration zone 22 need not necessarily be located near the top of the slurry bed 14 but can instead be located lower down since, should such bed slump occur, it has been found permanent clogging of the filter elements 30 will still not readily occur even if the elements are completely surrounded by settled solids or catalyst.

The elements 30 are preferably located with their outlets 40 directed downwardly so that any solid or catalyst fines which pass through the slots 46 with the filtrate (liquid product) will tend to collect in the bottom of the collection zones of the filter elements 30 from where they will be washed out with the liquid product.

To the outlet 40 of each of the filter elements 30 is connected a primary conduit 51, fitted with a restriction orifice 50. The conduits 51 of all the filter elements 30 making up a bank of the elements tie into a common secondary conduit 53 fitted with a shut-off valve 52. All the conduits 53 tie into a common tertiary conduit 54, fitted with a quick opening valve 56. A conduit 55 leads from the conduit 54 and is fitted with a shut-off or isolation valve 58. The conduit 55 leads into the top of a liquid blowdown vessel 60. A liquid rundown conduit 62, fitted with a shut-off valve 64, leads from the bottom of the vessel 60. The conduit 55 also serves as a backflushing conduit for gas. Alternatively, a liquid backflush conduit 66, fitted with a shut-off valve 68, can lead from the conduit 62, upstream of the valve 64, back to the conduit 54, between the valves 56, 58.

A pressurizing gas conduit or line 70, fitted with a control valve 72 leads into the top of the vessel 60, while a vent conduit or line 74, fitted with a control valve 76, leads from the top of the vessel 60.

In use, synthesis gas, comprising mainly carbon monoxide and hydrogen, enters the reactor vessel 12 along the flow line 18. The gas flow rate to the vessel 12 is such as to give a superficial gas velocity in the filtration zone 22, based on the open cross-sectional area of the filtration zone, of between 5 and 70 cm/s, typically about 30 to 40 cm/s.

In the reactor vessel 12, which is characterized thereby that it contains no mechanical mixing or agitation device such as a mechanical stirrer, the slurry bed 14 is maintained. As mentioned above, the slurry bed 14 comprises catalyst particles suspended in liquid product, ie liquid wax produced in the vessel 12 on reaction of the gaseous reactants. The catalyst particles are maintained in suspended state in the slurry bed 14, and in particular in the filtration zone 22, only by means of the turbulence created therein by the gas passing upwardly therethrough. This turbulence also inhibits excessive cake build-up on the filtering media, and thus enhances filtration through the media.

The catalyst can be any suitable Fischer-Tropsch synthesis catalyst, and can typically be an iron-based catalyst prepared by precipitation and spray-drying. The catalyst particle size distribution is such typically that there are no particles larger than 300 microns, while the fraction of particles smaller than 22 microns is typically less than 5% by volume of the catalyst loaded into the reactor vessel 12. However, it has been found that while the proportion of small particles, ie particles smaller than 22 microns, should be as low as possible, up to 40% by volume of such particles, based on total catalyst volume, can be tolerated. It has further been found that higher filtration rates are achievable when the content of particles smaller than 5 microns is minimized. However, it has been found that up to 25% by volume of such particles, based on total catalyst volume and measured in the end of run slurry, still gives satisfactory filtration rates. The mass percentage of catalyst in the catalyst/liquid product slurry of the slurry bed 14 is up to 40%.

The vessel 12 is typically maintained at an operating pressure of about 20 bar, and at an operating temperature between 180° C. and 260° C., typically about 240° C. However, the operating pressure can be in excess of 20 bar, and the operating temperature higher or lower than 240° C., as hereinbefore described, depending on the nature and spread of gaseous and liquid products required and the type of catalyst used. Naturally, the vessel 12 will be provided with suitable temperature control means, such as cooling coils for controlling the reaction temperatures, as well as suitable pressure control means such as a pressure control valve.

In the vessel 12, as the synthesis gas passes through the slurry bed 14, the carbon monoxide and hydrogen react to form a range of products in accordance with known Fischer-Tropsch reactions. Some of these products are in gaseous form at the operating conditions of the vessel 12 and are withdrawn, together with unreacted synthesis gas, along the flow line 20. Some of the products produced, such as the waxes already mentioned, are in liquid form at the operating conditions of the vessel 12, and act as the suspension medium for the catalyst particles. As liquid product is formed, the level 16 of the slurry bed naturally rises, and the liquid product is thus withdrawn in the filtration zone by means of the filter elements 30 and rundown vessel 60 to maintain the slurry bed level. This internal filtration constitutes a first stage of the operating cycle of the filter elements 30.

The liquid product which passes through the filter elements 30 and which contains a relatively small concentration of solids (catalyst) typically between 2 and 200 ppm, passes, by means of the conduits 53, 54 and 55 into the vessel 60. The vessel 60 is maintained, by means of pressurizing gas introduced along the line 70, at elevated pressure, which is, however, lower than that in the vessel 12. Typically, the pressure in the vessel 60 is set such that the pressure differential across the filtering media of the elements 30 and any filter cake build-up thereon, is about 4 bar.

In this fashion, a relatively constant slurry bed level in the reactor is maintained. However, when the filter cake has built up to some thickness, it must then be backflushed from the filtering media, in a second stage of the operating cycle of the filter elements 30. The backflushing is effected by shutting the quick opening valve 56 and valve 58, and withdrawing at least some of the liquid product in the rundown vessel 60, through the flow line 62, in order to remove any solids which have settled out in the bottom of the vessel 60. The pressure in the vessel 60 is then increased, by means of the gas pressurizing line 70, to a pressure greater than the operating pressure in the vessel 12. As a result of the static head of liquid (wax) in the rundown conduits, the liquid pressure at the quick opening valve 56 is typically slightly lower than the pressure in the vessel 60, but still sufficient for backflushing. When it is desired to backflush with liquid, the vessel 60 will thus contain some liquid product; however, if it is desired to backflush with gas, the vessel 60 will be pressurized with gas only, which can then be gaseous product such as tail gas.

Backflushing is effected in pulse-like fashion on one bank of filter elements 30 at a time, using either liquid product or gas. Thus, during backflushing, one of the valves 52 will be open, with the remaining valves 52 closed. For backflushing with liquid, valve 68 will be open, while for backflushing with gas, valve 58 will be open. In a first backflushing step, the quick opening valve 56 is opened rapidly in less than 0,8 seconds, and a volume of liquid product or gas, approximately equivalent to the internal volume of the filter elements 30 making up the bank of elements being flushed, is allowed to pass from the vessel 60, to produce a flow through the backflushing conduit 66 or 55, and the conduits 54, 53 and 51, thereby to provide flushing fluid through the bank of elements 30, in a second direction opposite to the direction in which the product flows during filtering. This typically takes up to 30 seconds. Thereafter, the quick opening valve 56 is again shut.

If a second backflushing step is desired, the vessel 60 is then again repressurized. In a second pulse-like backflushing step, the quick opening valve 56 is again opened rapidly for a second time. This time a flushing fluid volume equivalent to about one-third of the volume in the first backflushing operation, is allowed to pass from the vessel 60 to the filter elements 30. The valve 56 is thereafter again closed. If desired, at least one further similar backflushing step can be effected on that particular bank or filter elements.

Thereafter, the remaining banks of elements can similarly be backflushed, by opening and closing the appropriate valves 52.

In particular, rapid backflushing may be effected by using pressurized gas, which forces residual liquid product in the conduits through the filter elements in the second direction. Preferably, backflushing is then effected at least until backflushing gas starts passing through the restriction orifices. This leads to the advantages hereinbefore set out, viz effective cleaning of the filter element surfaces, and reducing extra loading of the filtering elements during filtration to no more than the volume of the residual liquid product in the conduits and filter elements, which is displaced during backflushing with the gas.

Without wishing to be bound thereby, it is believed that, during the first or initial backflushing step, any gas which has collected in the elements 30, is displaced by the backflushing fluid and some dislodging of the filter cake from the filtering media may be effected. During the subsequent backflushing step, dislodging and breaking up of the filter cake from the media by hydraulic action is primarily effected.

The flow rate of flushing fluid, during the first and second backflushing steps, is typically between 6000 and 9000 $l/h/m^2$ of filtering medium at a pressure differential of about 5 bar, and between 10000 and 12000 $l/h/m^2$ of filtering media at a pressure differential of about 10 bar, as hereinbefore described. The flow and distribution of the flushing fluid to the filter elements 30 of the bank of elements being flushed, is regulated by means of the restriction orifices 50, which typically have orifice sizes of about 7,5 mm, but the actual size depends on the flow per element and the number of elements per bank. The restriction orifices 50 thus serve to distribute the backflushing fluid evenly between the filter elements 30 of the bank being flushed.

Thereafter, in a third stage of the operating cycle of each bank of filter elements 30, they are subjected to a waiting period in which no liquid passes through them. The Applicant has found that the filtration rate, when the filter elements 30 are then thereafter again subjected to filtration as hereinbefore described, increases with an increase in the duration of the waiting or non-active period. However, this must be balanced against the disadvantage that the filter elements are out of service during these waiting times. It has been found that a waiting period of between 15 and 30 minutes gives good results. It is believed that, during this waiting period, catalyst which has been loosened from the filter media of the elements 30 and partially broken up during the backflushing stage, is effectively broken up further, removed from the filter media surfaces and re-mixed remotely from the filters 30, by means of the turbulence within the slurry bed 14. It is believed further that the gas superficial velocity through the filtration zone 22 may influence the optimum duration of the waiting period.

During the waiting period, gas is vented from the rundown vessel 60 by means of the line 74, in order to return the vessel 60 to the pressure required for the subsequent filtering operation.

It is believed that, by means of the internal filtration and backflushing as hereinbefore described, the slurry bed 14 can be maintained at relatively constant levels for prolonged periods of continuous operation. In pilot and commercial plant tests which have been conducted, it was found that the vessel 12 could operate reliably for several months with no permanent clogging of the filter elements 30 or mechanical failure thereof occurring. It may, however, be necessary to withdraw some slurry from time to time, and to add fresh catalyst, eg to maintain catalyst activity.

During the tests, it was also found that good instantaneous filtration rates, on average in excess of 500 $l/h/m^2$, were obtained, provided that the waiting period to which the filter elements were subjected was at least 15 minutes, and preferably about 30 minutes as hereinbefore described.

Figure 5:
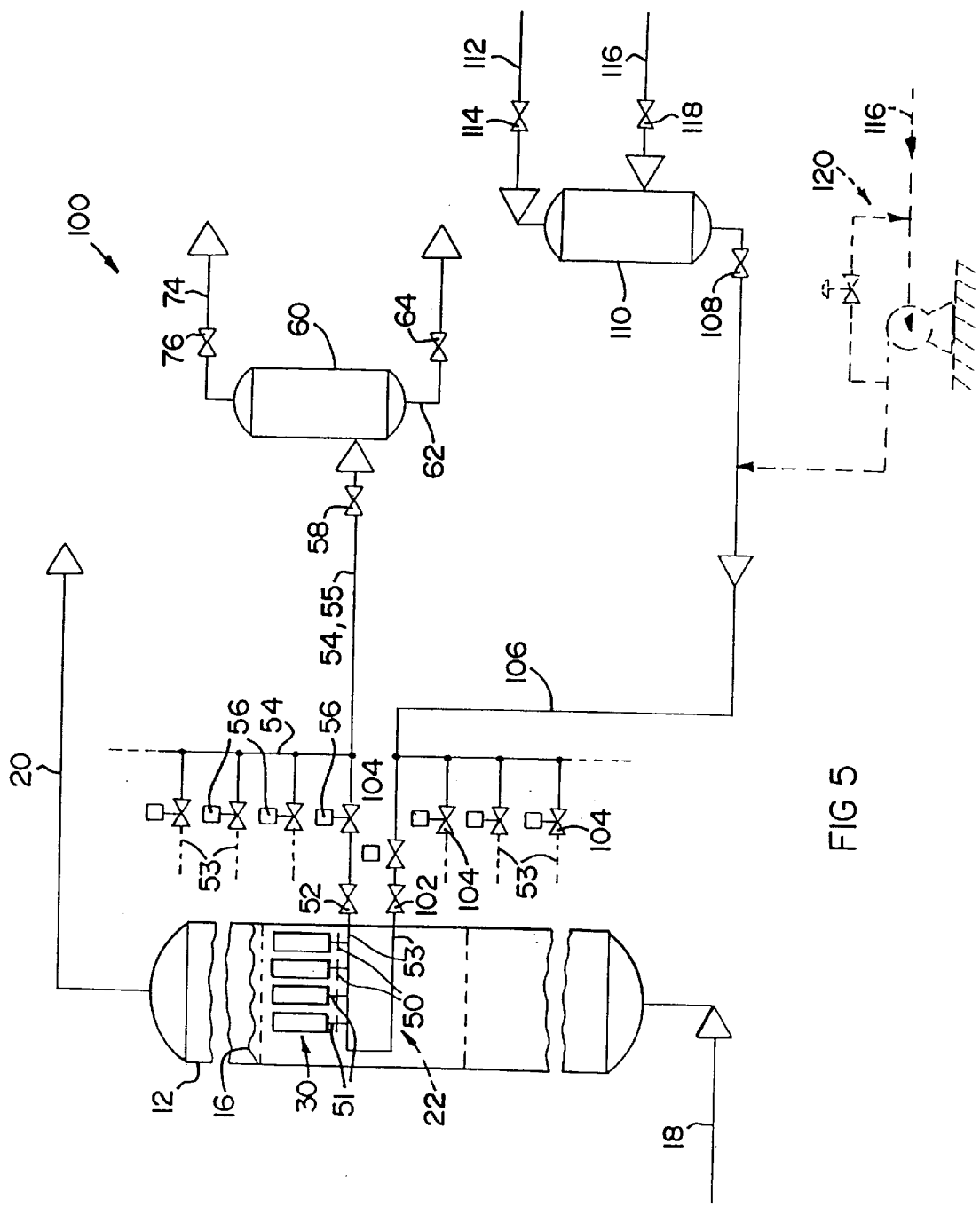
FIG. 5 shows a simplified flow diagram of an installation according to another embodiment of the invention, for producing gaseous and liquid products from gaseous reactants.

Referring to FIG. 5, reference numeral 100 generally indicates an installation according to another embodiment of the invention, for producing gaseous and liquid products from gaseous reactants.

Parts of the installation 100 which are the same or similar to those of the installation 10 hereinbefore described with reference to FIGS. 1 to 4, are indicated with the same reference numerals.

In the installation 100, each conduit 53 is provided with one of the quick opening valves 56, while the pressurizing conduit 70 for the vessel 60, and the backflush conduit 66 are dispensed with. Instead, each of the conduits 53 is in the form of a loop, with the valve 56 provided near one end of the loops, and valves 102, 104, which are similar to the valves 52, 56 respectively, near another end of the loop. The conduits 53 also tie into a common backflush fluid conduit 106, which leads from a backflush fluid vessel 110, and is fitted with a valve 108. A gas pressurizing line 112, fitted with a valve 114, leads into the vessel 110, as does a backflush liquid feed line 116, fitted with a valve 118.

For liquid backflush, the vessel 110 is supplied, by means of the flow line 116, with backflush liquid which can be, but is not limited to, filtered wax from the vessel 60. The pressure in the vessel 110 is maintained at a pressure which is preferably at least 5 bar higher than the pressure in the reactor vessel 12 by means of gas introduced along the flow line 112. The rate at which gas is introduced is preferably sufficient to prevent a drop in pressure in the vessel 110 of more than 1 bar during backflushing.

For gas backflush, no liquid is supplied to the vessel 110 which is thus filled only with gas, eg tail gas, introduced along the flow line 112.

Backflushing is effected on one bank of filter elements 30 while maintaining filtration through the remaining banks, by closing the filtration valve 56 of that bank. This is followed by rapid opening, preferably in less than 1 second, of the backflush valve 104 of that bank of elements. The backflush valve 104 remains open for a period which is sufficient for the required volume of backflush fluid to flow out of the backflush vessel 110 along the conduit 106, and is thereafter closed. Once the pressure in the backflush vessel has been restored by means of gas, the backflushing can be repeated on the same filter bank, or on the next bank of element by opening and closing the required filtering valves 56, and opening the appropriate backflush valve 104.

If desired, instead of using the backflush vessel 110, a pump 120, fitted with a controlled kickback loop, for liquid backflush, or a compressor (not shown) for gas backflush, can be used, as indicated in broken line in FIG. 5.

In known slurry bed reactors in which gas is subjected to catalytic reaction, separation of liquid product from catalyst particles is effected externally, ie some of the slurry is removed from the reactor vessel, and all or part of the liquid separated therefrom outside the reactor vessel, with the residue, which is then a dry catalyst or a slurry more concentrated in solids, returned to the reactor vessel. This separation can be by means of external hydrocyclones or magnetic separation devices. However, such an arrangement has the drawbacks of requiring a multiplicity of hydrocyclones with resultant multiplicity of pipes, valves and pumps, resulting in high capital costs. Furthermore, the separation is normally only partial, and hydrocyclones are prone to erosion so that high maintenance and operating costs arise.

Instead, the withdrawn slurry can be subjected to external decantation, ie the solids allowed to settle under quiescent conditions, and the resultant clarified liquid product decanted. However, such decantation is slow, requires large high pressure vessels which need to be operated isothermally to prevent remixing due to convection, separation is usually incomplete, pumps are required, capital costs are high, and a large catalyst inventory is required.

Yet further, external filtration equipment can be used. However, this is also capital intensive in view of the considerable piping and number of external vessels required. Furthermore, the slurry needs to be transferred to the filtration equipment by means of pumps, syphons or pressure drops, which affect catalyst quality negatively. The handling of slurries from the reactor to the filtration equipment, and of thick slurries from the filtration equipment back to the reactor, is cumbersome and requires substantial mechanical equipment, instrumentation and control equipment, which is capital intensive and also leads to high operating costs.

It is believed that the installations 10, 100 with the internal filtration, apart from having the advantages hereinbefore set out, also have the following advantages over the known external separating means as hereinbefore described, such as slurry and catalyst handling and transfer systems and equipment in the form of pipes, pumps and tanks are largely eliminated, since the filter cakes are formed on the filter elements inside the reactor and, on backflushing, are directly dispersed back into the slurry bed of the reactor;

the re-slurrying of the filter cake, which requires some effort, is easily effected through the natural turbulence present in the slurry bed in the reactor, as a result of the gas bubbling through the slurry bed;

the filter elements 30 and filter cakes are at all times kept at process conditions which, in the slurry bed 14, are practically isothermal;

in the known reactors, should there be unplanned shutdowns, slurries and high melting point liquids (waxes) in external filtration equipment can easily solidify on cooling, causing blockages; in the installations 10, 100 it is easier to keep the reactor vessel 12 at a sufficiently high temperature to prevent such cooling down, or to drain it, thereby substantially reducing the risk of blockages of filters;

in the installations 10, 100, the catalyst inventory is kept to a minimum, ie catalyst costs are minimized, since backflushing of the internal filter elements 30 occurs frequently enough to prevent excessive build-up, and hence temporary "loss", of catalyst in the filter cake;

the catalyst in the filter cakes in the installations 10, 100, and the liquid products, are always at the reactor process conditions, and there is thus reduced risk of deactivation of the catalyst and deterioration of the products, which can occur when external separation equipment is used and in which it is difficult to maintain these conditions;

being able to minimize the period that liquid products are kept external to the reactor at the high temperature prevailing in the reactor 12 and which could otherwise lead to a deterioration of liquid product quality if subjected to these high temperatures for longer periods.

We claim:

1. A process for producing liquid and, optionally, gaseous hydrocarbon products from gaseous reactants, which process comprises feeding gaseous reactants capable of reacting to form a liquid hydrocarbon product, into a slurry bed of catalyst particles suspended in a suspension liquid;

as the gaseous reactants pass upwardly through the slurry bed, allowing them to react at elevated temperature and at elevated pressure sufficient to form the liquid hydrocarbon product and, optionally, a gaseous hydrocarbon product;

separating the liquid hydrocarbon product from the catalyst particles by passing, in a filtration zone within the slurry bed, the liquid hydrocarbon product through a filtering medium in a first direction, so that a cake of solid catalyst particles forms on the filtering medium, while maintaining through the filtration zone a superficial gas velocity sufficient to maintain the slurry bed in a state of suspension and while applying a pressure differential across the filtering medium and the cake;

interrupting the passage of liquid hydrocarbon product through the filtering medium;

backflushing the filtering medium by passing a flushing liquid through the filtering medium in a second direction, opposite to the first direction, for a sufficient period of time and at a sufficient flushing liquid flow rate, while maintaining a pressure differential across the filtering medium and any filter cake build-up thereon, to dislodge the cake from the filtering medium;

subjecting the filtering medium to a waiting period during which no filtering or backflushing therethrough takes place, to permit further removal of the filter cake as a result of turbulence within the slurry bed; and again passing liquid hydrocarbon product through the filtering medium in the first direction so that a cake of solid catalyst particles again forms on the filtering medium.

2. A process according to claim 1, wherein the slurry bed is provided in a reactor vessel, with unreacted reactants and any gaseous product being withdrawn from the vessel above the slurry bed, and the separated liquid hydrocarbon product also being withdrawn from the vessel, the slurry bed being characterized thereby that at least its filtration zone is not mechanically mixed, with the catalyst particles in at least the filtration zone of the slurry bed thus being maintained in suspension by the turbulence created by the gaseous reactants passing through the slurry bed.

3. A process according to claim 2, wherein a plurality of the filtering media, arranged in banks, are provided, each filtering medium being provided by an elongate filter element mounted in the vessel and comprising the filtering medium which is in cylindrical form and a filtrate outlet for withdrawing liquid hydrocarbon product at one end thereof.

4. A process according to claim 3, wherein the pressure differential is effected by withdrawing the liquid product into a rundown vessel which is at a lower pressure than the reactor vessel, with the filtrate outlets of the filter elements being connected to the rundown vessel by means of liquid product conduits, with the flushing liquid being liquid product.

5. A process according to claim 4, wherein the backflushing is effected in pulse-like fashion, with an initial pulse of flushing liquid, followed by at least one further pulse of flushing liquid.

6. A process according to claim 5, wherein (i) each backflushing pulse comprises initiating flow of flushing liquid rapidly; and backflushing the elements rapidly with a volume of the flushing liquid; and (ii) during at least one of the backflushing pulses, the residual liquid product is forced through restriction orifices in the liquid product conduits.

7. A process according to claim 1, wherein the waiting period during which no filtering or backflushing takes place is up to 60 minutes.

8. A process according to claim 1, wherein the liquid and any gaseous products are hydrocarbon products; wherein the pressure differential across the filtering medium and the cake during separation of the liquid product from the catalyst particles is up to 8 bar, and wherein, during the backflushing, the backflushing period is up to 30 seconds, the flushing liquid flow rate is at least 6000 l/hr/m$^2$ of filtering medium, and the pressure differential which is maintained is up to 10 bar.

9. A process for producing liquid and, optionally, gaseous products from gaseous reactants, which process comprises feeding gaseous reactants capable of reacting to form a liquid product, into a slurry bed of catalyst particles suspended in a suspension liquid;

as the gaseous reactants pass upwardly through the slurry bed, allowing them to react at elevated temperature and at elevated pressure sufficient to form the liquid product and, optionally, a gaseous product;

separating the liquid product from the catalyst particles by passing, in a filtration zone within the slurry bed, the liquid product through a filtering medium in a first direction, so that a cake of solid catalyst particles forms on the filtering medium;

interrupting the passage of liquid product through the filtering medium;

backflushing the filtering medium by passing a flushing fluid through the filtering medium in a second direction, opposite to the first direction, thereby to dislodge the cake from the filtering medium;

subjecting the filtering medium to a waiting period during which no filtering or backflushing therethrough takes place, to permit further removal of the filter cake as a result of turbulence within the slurry bed; and again passing liquid product through the filtering medium in the first direction so that a cake of solid catalyst particles again forms on the filtering medium.

10. A process according to claim 9, wherein the liquid and any gaseous products are hydrocarbon products; wherein, during the separating of the liquid product from the catalyst particles, a superficial gas velocity of between 5 and 70 cm/s, based on the filtration zone open cross-sectional area is maintained, and a pressure differential of up to 8 bar is applied across the filtering medium and the cake; and wherein, during the backflushing, the backflushing is effected for up to 30 seconds, a flushing fluid flow rate of at least 6000 l/hr/m$^2$ of filtering medium is used, and a pressure differential across the filter medium and any filter cake build-up thereon of up to 10 bar is maintained.

11. A process according to claim 9, wherein the slurry bed is provided in a reactor vessel, with unreacted reactants and any gaseous product being withdrawn from the vessel above the slurry bed, and the separated liquid product also being withdrawn from the vessel, the slurry bed being characterized thereby that at least its filtration zone is not mechanically mixed, with the catalyst particles in at least the filtration zone of the slurry bed thus being maintained in suspension by the turbulence created by the gaseous reactants passing through the slurry bed.

12. A process according to claim 11, wherein a plurality of the filtering media, arranged in banks, are provided, each filtering medium being provided by an elongate filter element mounted in the vessel and comprising the filtering medium which is in cylindrical form and a filtrate outlet for withdrawing liquid product at one end thereof.

13. A process according to claim 12, wherein the pressure differential is effected by withdrawing the liquid product into a rundown vessel which is at a lower pressure than the reactor vessel, with the filtrate outlets of the filter elements being connected to the rundown vessel by means of liquid product conduits, with the flushing fluid being liquid product and/or gaseous product.

14. A process according to claim 13, wherein the backflushing is effected in pulse-like fashion, with an initial pulse of flushing liquid product and/or gaseous product, followed by at least one further pulse of flushing liquid product and/or gaseous product.

15. A process according to claim 14, wherein (i) each backflushing pulse comprises initiating flow of flushing fluid rapidly; and backflushing the elements rapidly with a volume of the flushing fluid; (ii) the backflushing includes, during the initial pulse, forcing residual liquid product in the liquid product conduits through the filter elements in the second direction, by means of pressurized gas; and (iii) during at least one of the backflushing pulses, the residual liquid product is forced through restriction orifices in the liquid product conduits.

16. A process according to claim 9, wherein the waiting period during which no filtering or backflushing takes place is up to 60 minutes.

\* \* \* \* \*